United States Patent [19]

Stolzer et al.

[11] 4,013,677

[45] Mar. 22, 1977

[54] PREPARATION OF 1,2,4-TRIAZOLYL-(1)-PHENOXY-ACYL-METHANES

[75] Inventors: Claus Stolzer; Wolfgang Kramer; Karl Heinz Büchel; Werner Meiser, all of Wuppertal, Germany

[73] Assignee: Bayer Aktiengesellschaft, Leverkusen, Germany

[22] Filed: Feb. 5, 1975

[21] Appl. No.: 547,429

[30] Foreign Application Priority Data

Feb. 12, 1974  Germany ............... 2406665

[52] U.S. Cl. .......................... 260/308 R
[51] Int. Cl.² ........................ C07D 249/08
[58] Field of Search ............... 260/308 R

[56] References Cited

UNITED STATES PATENTS 3,912,752  10/1975  Meiser et al. ............... 260/308 R Primary Examiner—Donald G. Daus
Assistant Examiner—Diana G. Rivers
Attorney, Agent, or Firm—Burgess, Dinklage & Sprung

[57] ABSTRACT

A process for the preparation of a 1,2,4-triazolyl-(1)-phenoxy-acyl-methane of the formula

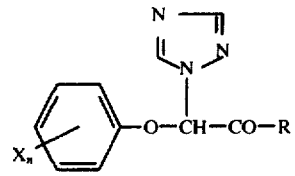

in which
R is alkyl or aryl,
each X independently is alkyl, halogen, alkoxycarbonyl, nitrile, phenyl or nitro, and
n is an integer from 0 to 5, comprising reacting a dihaloketone of the formula
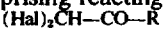
in which
Hal is halogen,

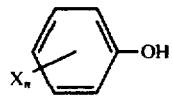

1,2,4-triazole and with a phenol of the formula t,0011 in the presence of an acid-binding agent and diluent, at a temperature of about 0° to 150° C. Advantageously the temperature is about 50° to 90° C and about 1 mole of the phenol, about 1 to 1.2 moles of the 1,2,4-triazole and about 2 to 3 moles of the acid-binding agent are used per mole of the dihaloketone.

10 Claims, No Drawings

PREPARATION OF 1,2,4-TRIAZOLYL-(1)-PHENOXY-ACYL-METHANES

It has already been disclosed in German Published Specification DOS 2,201,063 that 1,2,4-triazole derivatives, for example 1-[1',2',4'-triazolyl-(1')]-1-(4''-chlorophenoxy)-3,3-dimethyl-butan-2-one, can be prepared by the following processes:

a. Ketone-acetals are heated with 1,2,4-triazole hydrochloride to 220° C and the base is liberated from the resulting hydrochloride by means of sodium hydroxide solution in the usual way. However, this process has the disadvantage that the high reaction temperature leads to by-products, so that the yield is lowered. Furthermore, the need to liberate the base from the hydrochloride involves an additional reaction step.

1,2,4-Triazole derivatives are obtained when (b) haloether-ketones are reacted with 1,2,4-triazole, or when hydroxyether-ketones are either (c) reacted, with elimination of water, with 1,2,4-triazole at elevated temperature or (d) reacted with thionyl- or carbonyl-bis-1,2,4-triazole, 1,2,4-triazole and sulfur dioxide or carbon dioxide being split off.

Process (b) has the disadvantage that organic acid-binding agents are used which, when present in excess, cannot always be removed easily from the reaction mixture. Process (c) can only be carried out at an elevated temperature, and this in turn leads to a series of by-products. Furthermore, the water produced in the reaction must constantly be removed from the equilibrium in order to exclude a reverse reaction. In process (d), a starting product which is difficult to obtain and does not keep long, namely the bis-triazole mentioned, is used. Furthermore, the starting compounds are not easy to prepare in the case of all processes (b) to (d), all of which are multi-stage processes, and therefore the yields, calculated up to the final stage, are very low. Where more than 4 stages are involved, the overall yield is less than 50% of theory.

The present invention provides a new, surprising and advantageous process for the production of 1,2,4-triazolyl-(1)-phenoxy-acyl-methanes of the formula

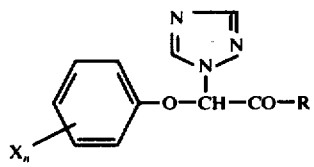

(I)

in which
R is alkyl or aryl,
each X independently is alkyl, halogen, alkoxycarbonyl, nitrile, phenyl or nitro, and
n is an integer from 0 to 5,
in which a dihaloketone of the formula (Hal)$_2$CH—CO—R　　　　II.

in which
Hal is halogen,
is reacted with 1,2,4-triazole and with a phenol of the formula

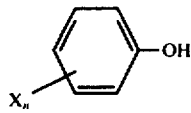

(III)

in the presence of an acid-binding agent and of a solvent or diluent, at a temperature of about 0° to 150° C.

It is very surprising that, by the reaction of the invention, assymmetrically substituted O,N-acetals are produced in one reaction step, because the knowledge in the art would have led one to expect that such a process would give a mixture of acetals and aminals. Furthermore, from Houben-Weyl, "Methoden organischen Chemie" ("Methods of Organic Chemistry"), Volume 6/3, pages 139 and 194/195 and 239/241, Georg-Thieme-Verlag, Stuttgart (1965), it was not to be expected that it would be possible to carry out the reaction according to the invention at a low reaction temperature.

The process according to the invention displays a series of advantages. The starting products are commercially available. The reaction is easy to carry out. The reaction products may be obtained in high purity and in good yields. Furthermore, the preliminary stages required for processes (b) to (d) have been made superfluous by the reaction according to the invention, so that the one-stage process according to the invention is much more economical.

If dichloropinacoline, 1,2,4-triazole and 4-chlorophenol are used as starting materials, the course of the reaction can be represented by the following formula scheme:

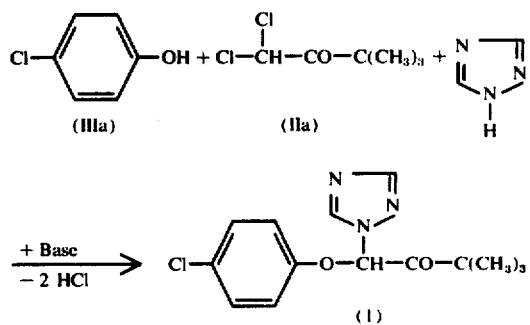

The formula (II) provides a general definition of the dihaloketones to be used as starting products. R preferably represents straight-chain or branched lower alkyl with 1 to 4 carbon atoms or phenyl. Hal preferably represents chlorine and bromine, especially chlorine. Dichloropinacoline, dibromopinacoline, dichloroacetophenone and dibromoacetophenone, disclosed in Beilstein's Handbuch der organischen Chemie (Beilstein's Handbook of Organic Chemistry), H 1,695, E, III 2842/43 and H 7, 282,286, E III 972, 985, are examples of compounds of formula (II) which can be used in the practice of the invention.

The phenols to be used as starting products are defined by formula (III). X preferably represents straight-chain or branched lower alkyl with up to 4 carbon atoms, halogen (especially chlorine, fluorine or bromine), alkoxycarbonyl with 1 or 2 carbon atoms in the alkoxy part, phenyl, nitrile and/or nitro. n is preferably 0, 1, 2 or 3. The compounds of formula (III) are generally known. The following may be mentioned as examples: 4-chlorophenol, 2,4-dichlorophenol, 2-chlorophenol, 4-bromophenol, 4-fluorophenol, 4-nitrophenol, 2-chloro-4-bromophenol, 1,2-cresol, 1,4-cresol, 1,3-cresol, 1,3,4-xylenol, 1,3,2-xylenol, 1,2,4-xylenol and 1,3,5-xylenol.

Polar solvents can be used as the diluent for the reaction. Preferred solvents include chlorinated hydrocarbons, for example dichlorethane; alcohols, for example ethanol, propanol, n-butanol and tert.-butanol; ketones, for example methyl ethyl ketone, methyl butyl ketone and acetone; ethers, for example tetrahydrofuran and dioxane; and nitriles, for example acetonitrile.

The reaction accordng to the invention is carried out in the presence of an acid acceptor. In general, an inorganic or organic acid-binding agent is used. The following may be mentioned as preferred inorganic acid-binding agents; alkali metal hydroxides, for example sodium hydroxide and potassium hydroxide; alkali metal carbonates, for example sodium carbonate and potassium carbonate; alkaline earth metal hydroxides, for example calcium hydroxide, magnesium hydroxide and barium hydroxide; and alkaline earth metal carbonates, for example barium carbonate or calcium carbonate. Tertiary amines, such as triethylamine or dimethylcyclohexylamine, may be mentioned as preferred organic acid-binding agents.

The process according to the invention is carried out at temperatures of about 0° to 150° C, preferably about 50° to 90° C.

In carrying out the process according to the invention, about 1 mole of phenol, 1–1.2 moles of 1,2,4-triazole and 2–3 moles of acid binding agent are generally employed per mole of dihaloketone. A further excess of the proportion of acid acceptor produces no significant improvement in yield. To isolate the active compounds according to the invention, the solvent may, if appropriate, be largely distilled off in vacuo. The residue may be treated with a little dilute hydrochloric acid in the presence of an inert water-immiscible solvent, for example toluene, xylene or dichloroethane, in order to remove excess triazole as the hydrochloride. Thereafter, the organic phase may be treated with dilute alkali metal hydroxide solution, as a result of which any unreacted phenol is removed as the phenolate. Thereafter, the organic phase is washed until neutral and the solvent is distilled off in vacuo. The residue can be purified by recrystallization or by counter-current steam distillation, optionally directly from the organic phase which has been washed until neutral.

The active compounds according to the invention display a very good fungitoxic activity as set forth in patent application Ser. No. 318,963, filed Dec. 27, 1972, now U.S. Pat. No. 3,912,752, the disclosure of which is incorporated herein by reference. The compounds can be used particularly successfully as plant protection agents against powdery mildew.

The present invention is illustrated by the following Examples.

EXAMPLE 1

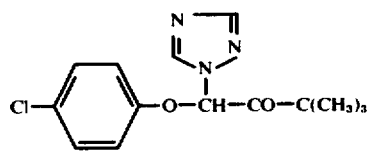

69.5 g (1.0 mole) of 1,2,4-triazole, 128.5 g (1.0 mole) of 4-chlorophenol and 353 g (2.55 moles) of anhydrous powdered potassium carbonate are taken up in 1,000 ml of acetone. 186 g (1.1 moles) of dichloropinacoline are added dropwise at room temperature. The mixture is boiled for 15 hours under reflux while stirring and is concentrated in a water pump vacuum after cooling and filtering with suction. The residue is taken up in 500 ml of toluene, and a mixture of 40 ml of concentrated hydrochloric acid and 500 ml of water is added, whereupon any unreacted triazole goes into solution as triazole hydrochloride. Thereafter, the organic phase is treated with a solution of 40 ml of concentrated sodium hydroxide solution in 500 ml of water, Whereupon, any unreacted phenol dissolves as the phenolate. Thereafter, the organic phase is washed until neutral, dried and concentrated. 225 g of 1-[1',-2',4'-triazolyl-(1')]-1-(4''-chlorophenoxy)-3,3-dimethyl-butan-2-one of melting point 74° – 76° C are obtained. The yield is 76.8% of theory.

EXAMPLE 1a

If working on a larger scale is intended, the following procedure is used:

24.6 kg (340 moles) of 1,2,4-triazole, 120 kg (870 moles) of anhydrous powdered potassium carbonate, and 43.6 kg (340 moles) of 4-chlorophenol are taken up in 134 kg of acetone. 64 kg (379 moles) of dichloropinacoline, dissolved in 27 kg of acetone, are added within 8 hours at a temperature of 70° C. The mixture is boiled for 16 hours under reflux while stirring. After cooling down to 20° C it is filtered off with suction, washed with 100 kg of acetone and concentrated in a water vapor jet vacuum. The residue is dissolved in 348 kg of toluene at a temperature of 70° C and stirred with a mixture of 113.4 kg of water and 5.7 kg of pure, concentrated hydrochloric acid, in doing so any unreacted triazole goes into solution as triazole hydrochloride. The organic phase is washed thereafter with 100 kg of water and once more stirred with a mixture of 190 kg of water and 18.2 kg of a 45% solution of caustic soda, whereupon any possibly unreacted phenol dissolves as the phenolate. Thereafter the organic phase is washed with several 100 kg portions of water until neutral. The toluene product phase is treated while stirring and cooling with water at 20° to 30° C with 97.4 kg (476 moles) of 47.9% sulfuric acid. During the addition the sulfate of the 1-[1',2',4'-triazolyl-(1')]-1-(4''-chlorophenoxy)-3,3-dimethyl-butan-2-one precipitates. The impurities remain dissolved. After suction the sulfate is washed with 131 kg of toluene. The toluene-wet salt is suspended in 228 kg of toluene and 300 kg of water, and 83.3 kg (937 moles) of a 45% solution of caustic soda are added to the dispersion while stirring and cooling in such a way that the temperature does not exceed 20° to 30° C. After continued stirring for 30 minutes, small quantities of suspended substances are sucked off and the toluene product phase is separated. Thereafter the organic phase is washed until neutral with several 200 kg portions of water and the solvent is distilled off at 80° C in a water vapor jet vacuum. There are obtained 71.0 kg of 1-[1',2',4'-triazolyl-(1')]-1-(4''-chlorophenoxy)-3,3-dimethyl-butan-2-one with a melting point of 74° C. The yield is 71.2% of the theory.

EXAMPLES 2 – 16

The following compounds of the formula

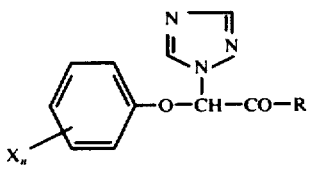

were prepared analogously to Example 1.

| Example | X | n | R | Boiling point Melting point |
|---|---|---|---|---|
| 2 | 2-CH₃, 5-Cl | 2 | C(CH₃)₃ | 114° C |
| 3 | 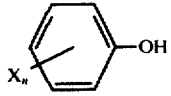-4 | 1 | C(CH₃)₃ | 105–106° C |
| 4 | 2,4-Cl₂ | 2 | C(CH₃)₃ | 65° C |
| 5 | 2-Cl | 1 | C(CH₃)₃ | 68–69° C |
| 6 | 2,6-Cl₂ | 2 | C(CH₃)₃ | 186° C |
| 7 | 4-Br | 1 | C(CH₃)₃ | 89–92° C |
| 8 | 4-F | 1 | C(CH₃)₃ | boiling point 0.3mm/160° C |
| 9 | 4-CH₃ | 1 | C(CH₃)₃ | 74–76° C |
| 10 | 4-NO₂ | 1 | C(CH₃)₃ | 145° C |
| 11 | 4-COOCH₃ | 1 | C(CH₃)₃ | 85–88° C |
| 12 | H | 0 | C(CH₃)₃ | 62° C |
| 13 | 2,3-(CH₃)₂ | 2 | C(CH₃)₃ | 76° C |
| 14 | 3,4-(CH₃)₂ | 2 | C(CH₃)₃ | 71° C |
| 15 | H | 0 | 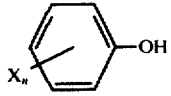 | 65–70° C |
| 16 | 2-Cl, 4-Br | 2 | C(CH₃)₃ | 94–96° C |

Other compounds which can be similarly prepared include:
1-[1',2',4'-triazolyl-(1')]-1-(4''-carboisopropoxyphenoxy)-propan-2-one,
1-[1',2',4'-triazolyl-(1')]-1-(pentachlorophenoxy)-ethan-2-one,
1-[1',2',4'-triazolyl-(1')]-1-(4''-cyanophenoxy)-3,3-dimethyl-butan-2-one,
1-[1',2',4'-triazolyl-(1')]-1-(2'',3'',6''-trichlorophenoxy)-3,3-dimethyl-butan-2-one,
1-[1',2',4'-triazolyl-(1')]-1-(4''-tert.butylphenoxy)-3,3-dimethyl-butan-2-one,
and the like.

It will be appreciated that the instant specification and examples are set forth by way of illustration and not limitation, and that various modifications and changes may be made without departing from the spirit and scope of the present invention.

What is claimed is:
1. A process for the preparation of a 1,2,4-triazolyl-(1)-phenoxy-acyl-methane of the formula

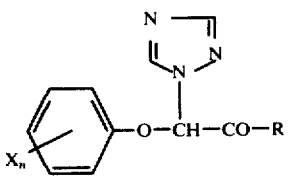

in which
R is alkyl with 1 to 4 carbon atoms or phenyl,
each X independently is alkyl with 1 to 4 carbon atoms, halogen, alkoxycarbonyl with 1 or 2 carbon atoms in the alkoxy, nitrile, phenyl or nitro, and
n is an integer from 0 to 5,
comprising reacting a dihaloketone of the formula (Hal)₂CH—CO—R in which
Hal is halogen,
with 1,2,4-triazole and with a phenol of the formula

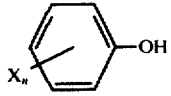—OH in the presence of an acid-binding agent selected from the group consisting of alkali metal and alkaline earth metal hydroxides and carbonates and tertiary amines and a polar organic solvent as diluent, at a temperature of about 0° to 150° C.

2. A process according to claim 1 in which the reaction is carried out at about 50° to 90° C.

3. A process according to claim 1 in which about 1 mole of the phenol, about 1 to 1.2 moles of the 1,2,4-triazole and about 2 to 3 moles of the acid-binding agent are used per mole of the dihaloketone.

4. A process according to claim 1, Hal is chlorine, each X independently is alkyl with 1 to 4 carbon atoms, chlorine, fluorine, bromine, alkoxycarbonyl with 1 or 2 carbon atoms in the alkoxy, phenyl, nitrile or nitro, and n is 0, 1, 2 or 3.

5. A process according to claim 4 in which the reaction is carried out at about 50° to 90° C, and about 1 mole of the phenol, about 1 to 1.2 moles of the 1,2,4-triazole and about 2 to 3 moles of the acid-binding agent are used per mole of the dihaloketone.

6. A process according to claim 1 in which R is tert. butyl and X is 4-chloro.

7. A process according to claim 1 in which R is tert. butyl and X is 4-phenyl.

8. A process according to claim 1 in which R is tert. butyl and X is 2,4-dichloro.

9. A process according to claim 1 in which R is tert. butyl and X is 4-bromo.

10. A process according to claim 1 in which R is tert. butyl and X is 4-fluoro.

* * * * *